US009804836B2

United States Patent
Gondek et al.

(10) Patent No.: US 9,804,836 B2
(45) Date of Patent: *Oct. 31, 2017

(54) MEDICAL DEVICE NUCLEUS ARCHITECTURE

(71) Applicant: Welch Allyn, Inc., Skaneateles Falls, NY (US)

(72) Inventors: Cory R. Gondek, Tigard, OR (US); Soundharya Nagasubramanian, Portland, OR (US); Paul S. Kovitz, Portland, OR (US); Charles Alfred, Nashua, NH (US); Dan E. Goldman, III, Shrewsbury, MA (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 139 days.

This patent is subject to a terminal disclaimer.

(21) Appl. No.: 14/535,401

(22) Filed: Nov. 7, 2014

(65) Prior Publication Data

US 2015/0378720 A1 Dec. 31, 2015

Related U.S. Application Data

(60) Provisional application No. 62/017,908, filed on Jun. 27, 2014.

(51) Int. Cl.
*G06F 9/44* (2006.01)
*A61B 5/00* (2006.01)
(Continued)

(52) U.S. Cl.
CPC .............. *G06F 8/70* (2013.01); *G06F 9/546* (2013.01); *G06F 19/3406* (2013.01);
(Continued)

(58) Field of Classification Search
CPC ........ G06F 8/70; G06F 9/546; G06F 19/3406; G06F 19/3412; A61B 5/01; A61B 5/021;
(Continued)

(56) References Cited

U.S. PATENT DOCUMENTS 5,170,465 A 12/1992 McKeeman et al.
5,768,505 A * 6/1998 Gilchrist et al. .............. 709/201
(Continued)

OTHER PUBLICATIONS

International Search Report and Written Opinion in PCT/US2015/037173 dated Sep. 30, 2015, 11pgs.

*Primary Examiner* — Qing Chen
(74) *Attorney, Agent, or Firm* — Merchant & Gould P.C.

(57) ABSTRACT

A medical software package stored on a non-transitory, computer-readable storage medium is disclosed. The medical software package can include a plurality of software components programmed to provide one or more functionalities to one or more medical monitoring devices, where each software component is programmed to run independently as a daemon, where each software component is programmed to be modified without recompiling unchanged software components, where the software components are programmed to communicate to each other through at least one of the software components, and where the software package is hardware agnostic and operating system agnostic. A medical device including a tangible, non-transitory storage device storing a medical software package comprising a plurality of modular software components programmed to provide medical device functionality is also disclosed.

4 Claims, 7 Drawing Sheets

(51) Int. Cl.
*G06F 19/00* (2011.01)
*G06F 9/54* (2006.01)
*A61B 5/01* (2006.01)
*A61B 5/021* (2006.01)
*A61B 5/024* (2006.01)
*A61B 5/145* (2006.01)

(52) U.S. Cl.
CPC ............ *G06F 19/3412* (2013.01); *A61B 5/01* (2013.01); *A61B 5/021* (2013.01); *A61B 5/024* (2013.01); *A61B 5/14542* (2013.01); *A61B 2560/0437* (2013.01)

(58) Field of Classification Search
CPC ................ A61B 5/024; A61B 5/14542; A61B 2560/0437
USPC .......................... 717/120–123; 600/300, 301
See application file for complete search history.

(56) References Cited

U.S. PATENT DOCUMENTS

| | | | |
|---|---|---|---|
| 6,751,463 B1* | 6/2004 | Lorello | H04L 51/22 455/412.1 |
| 2001/0025371 A1* | 9/2001 | Sato et al. | 717/4 |
| 2001/0044732 A1 | 11/2001 | Maus et al. | |
| 2002/0012329 A1* | 1/2002 | Atkinson et al. | 370/330 |
| 2002/0026631 A1* | 2/2002 | Barritz | 717/127 |
| 2002/0059369 A1 | 5/2002 | Kern et al. | |
| 2002/0188211 A1 | 12/2002 | Voith | |
| 2003/0018959 A1* | 1/2003 | Wallman et al. | 717/148 |
| 2003/0056193 A1* | 3/2003 | Perycz et al. | 717/107 |
| 2003/0217359 A1* | 11/2003 | Ohi et al. | 717/174 |
| 2004/0133887 A1* | 7/2004 | Herle et al. | 717/171 |
| 2004/0236610 A1* | 11/2004 | Nagaoka et al. | 705/3 |
| 2005/0060392 A1* | 3/2005 | Goring | G06F 9/4443 709/220 |
| 2005/0076098 A1* | 4/2005 | Matsubara et al. | 709/219 |
| 2005/0076326 A1 | 4/2005 | McMillan et al. | |
| 2005/0159787 A1 | 7/2005 | Linberg et al. | |
| 2007/0074191 A1* | 3/2007 | Geisinger | 717/148 |
| 2008/0114852 A1 | 5/2008 | Claus et al. | |
| 2008/0155494 A1 | 6/2008 | Gobel | |
| 2009/0030969 A1* | 1/2009 | Dutta et al. | 709/201 |
| 2009/0172640 A1* | 7/2009 | Geismar et al. | 717/121 |
| 2009/0177180 A1* | 7/2009 | Rubalcaba et al. | 604/500 |
| 2009/0276480 A1* | 11/2009 | Anna et al. | 709/201 |
| 2011/0320840 A1 | 12/2011 | Nayar et al. | |
| 2014/0149520 A1* | 5/2014 | Granshaw et al. | 709/206 |
| 2014/0155771 A1 | 6/2014 | Quick et al. | |
| 2015/0378720 A1 | 12/2015 | Gondek | |
| 2015/0378798 A1 | 12/2015 | Gondek | |

* cited by examiner

MEDICAL DEVICE NUCLEUS ARCHITECTURE

CROSS REFERENCE TO RELATED APPLICATIONS

This application claims priority to U.S. Ser. No. 62/017,908, titled Nucleus Architecture, filed on Jun. 27, 2014, the disclosure of which is hereby incorporated by reference in its entirety.

BACKGROUND

Many medical devices require software in addition to a measurement component for their operation. Devices developed and released at different times can have different software versions that may not be compatible to communicate with other devices or to a central monitoring unit. Also, a software architecture where software items cannot be reused, or where a change to one software component requires changes to all software components, can inhibit the pace of development and can increase the cost of maintaining such a system.

SUMMARY

In one aspect, a medical software package stored on a non-transitory, computer-readable storage medium is disclosed. The software package can include a plurality of software components programmed to provide one or more functionalities to one or more medical monitoring devices, wherein each software component is programmed to run independently as a daemon, wherein each software component is programmed to be modified without recompiling unchanged software components, wherein the software components are programmed to communicate to each other through at least one of the software components, and wherein the software package is hardware agnostic and operating system agnostic.

The plurality of software components can further include a plurality of reusable assets, wherein one of the plurality of reusable assets is a workflow manager programmed to store, add, remove, start or stop manager programs, including scripts, resident in the storage medium and wherein one of the plurality of reusable assets is a capability registry programmed to provide a bulletin board system where software components can post common object-oriented architecture messages and receive messages about changes to any of the posted messages. Additionally, the reusable assets can include a virtual operating system programmed to provide a fixed application programming interface between the software components and an underlying operating system and a virtual hardware programmed to provide a fixed application programming interface between the software components and underlying hardware and device drivers.

In embodiments, the common object-oriented architecture messages can persist on the bulletin board until the first of: a system supporting the medical software package shuts down, the reusable asset that posted the message shuts down, or another message with the same identifier is posted to the bulletin board. Each of the common object-oriented architecture messages can have a unique identifier. The common object-oriented architecture messages can include information about one of the following: connected hardware, hardware manufacturer, and software version.

One of the plurality of reusable assets can be a configuration manager programmed to maintain persistent configuration of the device and provide a device configuration to client software components. The configuration manager can be programmed to persist configuration-based common object-oriented architecture messages through power cycles and to manage multiple versions of each configuration-based common object-oriented architecture message. One of the plurality of reusable assets can be a message manager programmed to provide an inter-process communications bus for sending common object-oriented architecture messages between the software components. Also, one of the plurality of reusable assets can be a component manager programmed to start up and shut down at least one of the software components.

In another aspect, a medical device comprising a tangible, non-transitory storage device storing a medical software package comprising a plurality of modular software components programmed to provide medical device functionality is disclosed. Each software component can be programmed to: run independently as a daemon, be modified without recompiling unchanged software components, and communicate to each other through at least one of the software components. The software package can be hardware agnostic and operating system agnostic and the plurality of software components can further comprise a plurality of reusable assets. One of the plurality of reusable assets can be a workflow manager programmed to store, add, remove, start or stop any program, including, but not limited to, manager scripts resident in the storage medium.

In yet another aspect, a non-transitory computer-readable storage medium storing a computer program for a medical device is disclosed. The computer program can include instructions executed by one or more processors mounted on the medical device, the instructions causing the one or more processors, when executed by the one or more processors to execute processes including providing a bulletin board wherein software components stored in the storage medium can post common object-oriented architecture messages and receive messages about changes to any of the posted messages and providing a workflow manager programmed to store, add, remove, start or stop manager programs, including scripts, resident in the storage medium. The common object-oriented architecture messages can persist on the bulletin board until the first of: a system supporting the medical software package shuts down, the reusable asset that posted the message shuts down, or another message with the same identifier is posted to the bulletin board. Each of the common object-oriented architecture messages can have a unique identifier.

DETAILED DESCRIPTION

Medical environments, such as clinics, hospitals, nursing homes, care facilities, and at-home care stations, can rely on peripheral devices that communicate, display, and coordinate the monitoring and maintenance of a patient's health. Having the software components of a particular model and make of a medical monitoring device associated with a monitoring system, such as a specific SpO$_2$ monitor, can limit the flexibility of the system with respect to future improvements or modifications. Moreover, it can be disadvantageous to use a fixed software architecture that requires propagating any change, minor or major, to every software component and service within the system. The instant disclosure is directed to a solution to the above-described limitations of current medical software systems.

As used herein, "medical device" refers to any device that can be used in a medical environment. Examples of medical devices include, but are not limited to, thermometers, blood pressure sensors, heart rate sensors, pulse rate sensors, SpO2 sensors, devices to monitor vital signs, devices for metering fluids, etc.

A first component is the low acuity vitals system architecture. The system architecture incorporates a compartmentalized design wherein each process can be run as a daemon and run separately. Thus, each process in the system is separate. Advantages of the system include, for example, that, unlike existing systems, if a change is made to the code of a process, the coding for each process does not need to be similarly adjusted. For example, if the code associated with a temperature process is changed, that change to the code does not need to be propagated to every other process in the system.

A second component is the nucleus architecture comprising separate applications. The nucleus architecture can be used to communicate information between separate software services which separates the interfaces of the services from the internal operation of the services. This structure can enable changes to individual services to be made without affecting the safety or operation of the other services. Additionally, the nucleus can also provide a base of functionality for saving data through device power cycles, starting services and monitoring the started services for functionality, providing a service where data can be stored temporarily such that other services can be restarted and retrieve the system state, and a service to provide dynamic scripted workflows to quickly respond to customer needs. The nucleus can enable communication between separate software services, which separates the interfaces of the services from the internal operation of the services. In a preferred embodiment, the nucleus is agnostic to the particular operating system.

Figure 1:
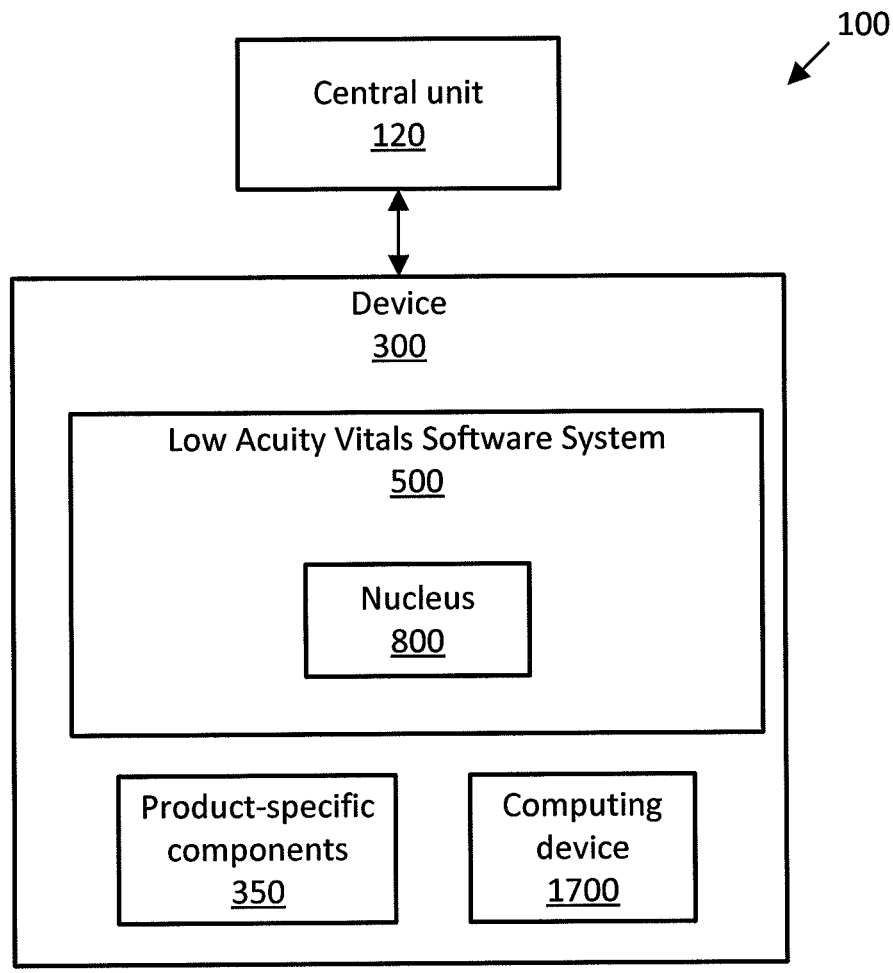
FIG. 1 illustrates a block diagram of an example medical device.

An example medical product system 100 is shown in FIG. 1. The example medical product system 100 includes an optional central unit 120, a device 300 comprising a computing device 1700 that includes product-specific software components 350, and a low acuity vitals software system 500, which includes a nucleus 800. Other embodiments may include more or fewer components.

In some embodiments, the device 300 can communicate via a wired or wireless protocol with the central unit 120. In some embodiments, the device 300 is the central unit 120. The central unit 120 can include a computing device, for example the computing device 1700 shown and described in detail with reference to FIG. 7, and a user interface which can include a display and input capability. In embodiments, the central unit 120 can display and/or control the example medical devices described herein.

In embodiments, the device 300 can be an external component, device, service, or service tool. The device 300 can include other product-specific components 350, such as sensor components in a thermometer, not shown. Additional examples and discussion of types of devices 300 are described in more detail with reference to peripherals 600, hardware 610 and services 620, below.

The low acuity vitals software system 500 (LAV architecture) is a software architecture used by the device 300. The low acuity vitals software system 500 includes a nucleus 800. The LAV architecture 500 is shown and described in more detail with reference to FIG. 4 below.

Example device 300 also includes a computing device 1700 for processing and communication. The computing device 1700 includes product-specific software components 350. The computing device 1700 is shown and described in more detail below with reference to FIG. 7.

Figure 2:
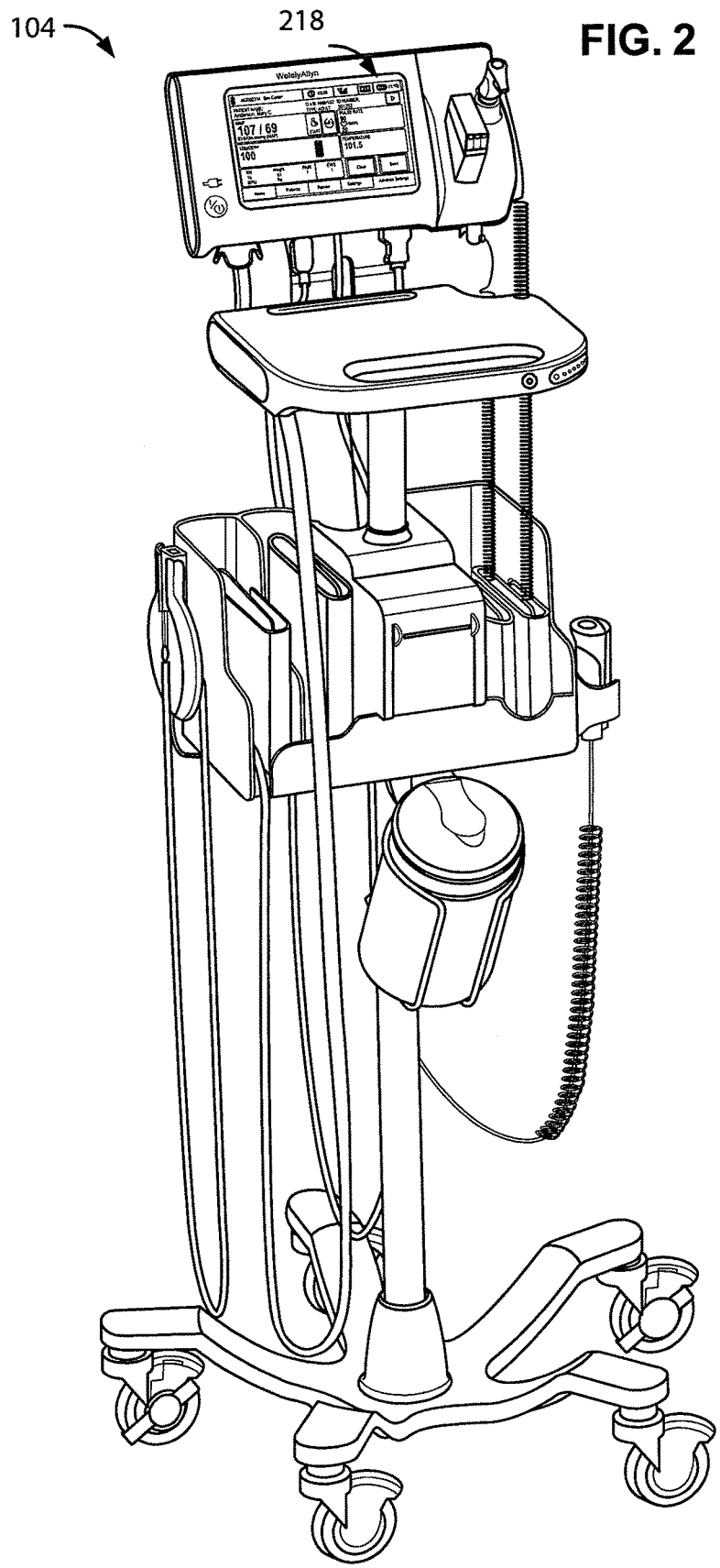
FIG. 2 illustrates an example medical device of FIG. 1.

FIG. 2 illustrates one example of the medical device 104. The medical device 104 is shown on a mobile cart, and the medical device 104 is programmed to provide the functionalities described herein. The medical device 104 includes a display screen 218 and includes the ability to execute multiple workflows or profiles. In some embodiments, the display screen 218 is a touch screen. Other embodiments can include more or fewer components than those shown in FIG. 2, or include different components that accomplish the same or a similar function.

The medical device 104 is able to operate within one or more profiles. A profile is a series of one or more tasks that a user of the medical device 104 performs. When the medical device 104 operates within a profile, the medical device 104 provides functionality suitable for assisting the user in performing the profile. When the medical device 104 operates within different profiles, the medical device 104 provides different functionality.

When the medical device 104 is manufactured, the medical device 104 is configured to be able to operate within one or more profiles. After the medical device 104 is manufactured, the medical device 104 can be reconfigured to operate within one or more additional profiles. In this way, a user can adapt the medical device 104 for use in different profiles as needed.

In various embodiments, the medical device 104 operates within various profiles. For example, in some embodiments, the medical device 104 can operate within an interval profile or a non-interval profile. Example types of non-interval profiles include, but are not limited to, a spot check profile, an office profile, and an interval profile. An example of an interval profile includes, but is not limited to, an intervals profile.

In example embodiments, the names for the profiles can be defined by the user. For example, the user can rename an "interval profile" as "ED 3 North" or any other nomenclature as desired to provide more context to the user.

When the medical device 104 is operating within the interval profile, the medical device 104 obtains a series of measurements of one or more physiological parameters of a single monitored patient over a period of time. In addition, the medical device 104 displays, on the display screen 218, an interval profile home screen. The interval profile home screen contains a representation of a physiological parameter of the monitored patient. The representation is based on at least one measurement in the series of measurements. A representation of a physiological parameter is a visible image conveying information about the physiological parameter.

For example, when the medical device 104 is operating within the interval profile, the medical device 104 can obtain a blood pressure measurement of a single patient once every ten minutes for six hours. In this example, the medical device 104 displays an interval profile home screen that contains a representation of the patient's blood pressure based on a most recent one of the blood pressure measurements. In this way, a user of the medical device 104 can monitor the status of the patient.

When the medical device 104 is operating within a non-interval profile, the medical device 104 obtains a measurement of one or more physiological parameters from each patient in a series of patients. In addition, the medical device 104 displays a non-interval profile home screen on the display screen 218. The non-interval profile home screen contains a representation of the physiological parameter of a given patient in the series of patients. The representation is based on the measurement of the physiological parameter of the given patient.

In one example, when the medical device 104 is operating within a spot check profile, the medical device 104 obtains blood pressure measurements from a series of previously-identified patients. In this other example, the medical device 104 displays a spot check profile home screen containing a blood pressure measurement of a given patient in the series of previously-identified patients. In this way, a user of the medical device 104 can perform spot checks on the blood pressures of patients who have already been admitted to a hospital.

As used in this document, a patient is a previously identified patient when the medical device 104 stores information regarding the identity of the patient. In another example, when the medical device 104 is operating within an interval profile, the medical device 104 can obtain a single blood pressure measurement from each patient in a series of unidentified patients as the patients arrive at a hospital.

The interval profile home screen may be different than the non-interval profile home screen. Further, as discussed below, the navigation options associated with the different profiles allows for efficient monitoring based on the environment in which the device is used. In various embodiments, the interval profile home screen is different than the non-interval profile home screen in various ways. For example, in some embodiments, the interval profile home screen includes at least one user-selectable control that is not included in the non-interval profile home screen. In other embodiments, a representation of a physiological parameter in the interval profile home screen has a different size than a representation of the same physiological parameter in the non-interval profile home screen.

Figure 3:
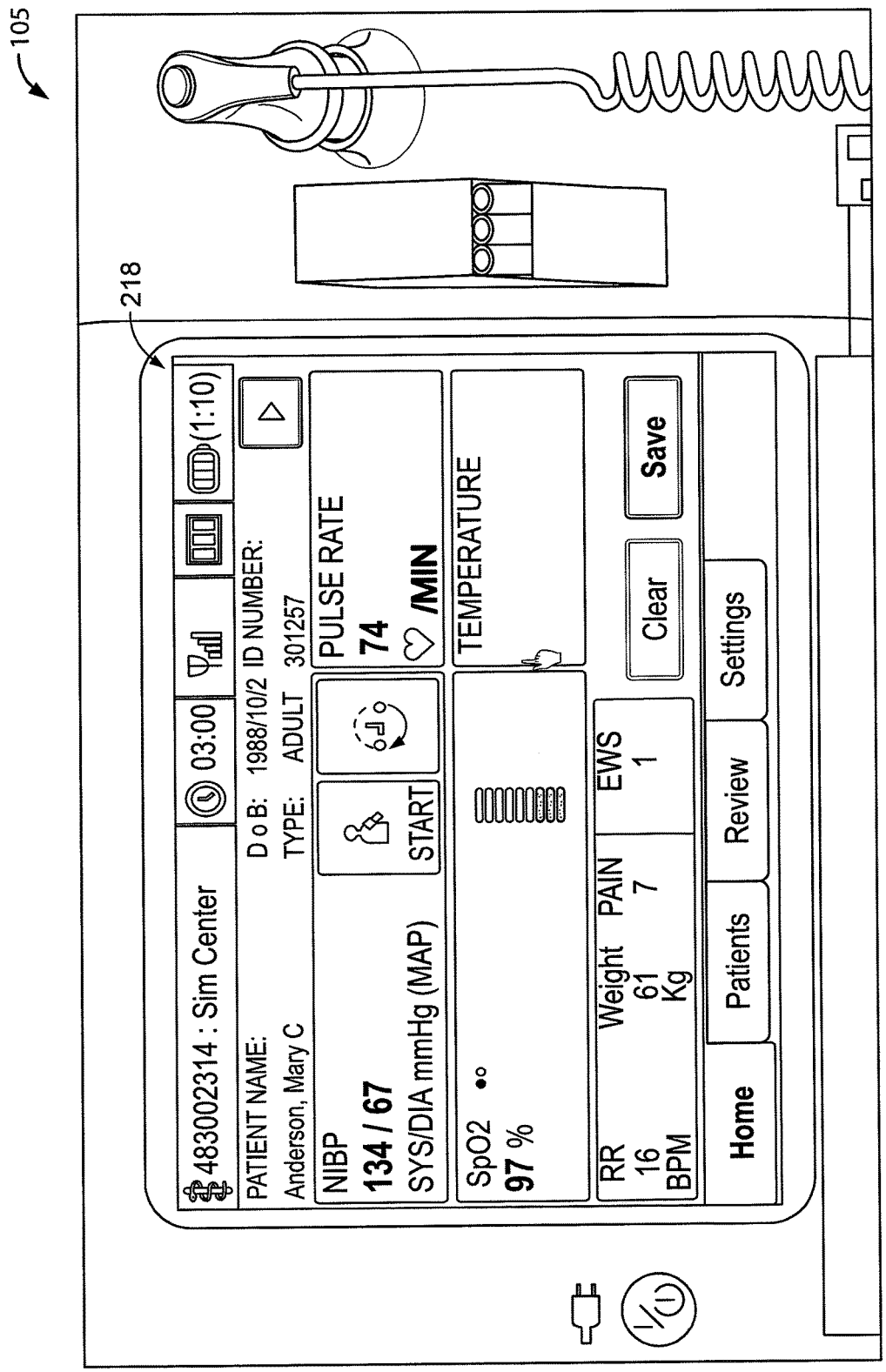
FIG. 3 illustrates another example medical device of FIG. 1.

An additional example of the medical device 105 is shown in FIG. 3. In this example, the medical device 105 is similar to that of the medical device 104 described above. In embodiments, the medical device 105 is mounted on a wall. The medical device 104 is programmed in a manner similar to that described above to monitor physiological parameters of a patient. In some embodiments, the medical device 105 is a stand-alone device, which can mean that is not part of a mobile cart and it is not part of a wall-mounted station.

In the examples described herein, the medical devices 104, 105, 106 are computing devices that have been programmed to perform special, complex functions. These specially-programmed devices function to manipulate and provide data to the users in an improved form factor and with greater efficiency.

For example, as described further below, the medical devices 104, 105, 106 are specially programmed to provide the user with an improved interface during initial use of the devices. This allows the user to more efficiently select a profile for controlling the functionality of the device.

In addition, the medical devices 104, 105, 106 are specially programmed to assist the users once vital signs information is captured from the patients. For example, the devices are programmed to more efficiently and easily capture additional contextual information that is needed when saving vital signs data to a permanent record, such as an EMR record. This is accomplished using an interface that is more intuitive and robust.

The medical devices 104 and 105 shown in FIGS. 2 and 3 are only examples of a medical device. In some examples described herein, the medical devices 104 and 105 are portable devices. In other examples, the medical devices 104 and 105 are non-portable devices, such as computing devices like workstations. All different types of medical devices used to collect patient data can be used. Many configurations are possible.

Figure 4:
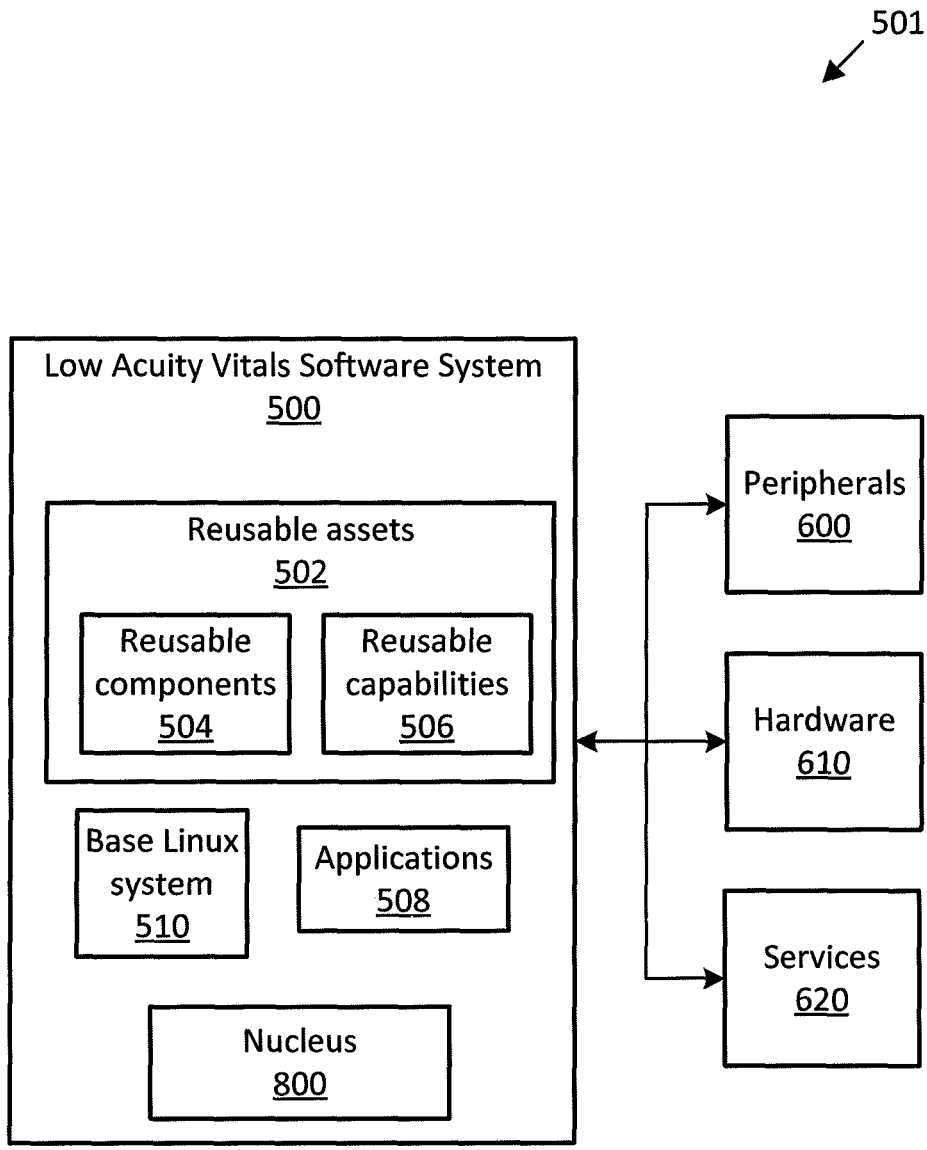
FIG. 4 illustrates a block diagram illustrating an example low acuity vitals software/hardware system.

FIG. 4 is a block diagram illustrating an example low acuity vitals (LAV) software/hardware system 501. The example system 501 includes the software components of an example low acuity vitals software system 500. Also shown are example components that can interact with the LAV system 500, such as peripherals 600, hardware 610 and services 620. The LAV system includes reusable assets 502, comprising reusable components 504 and reusable capabilities 506, a base Linux system 510, applications 508 and Nucleus 800. Other embodiments may include more or fewer components.

Example peripherals 600 can include a display, such as an LCD display, a saturation of peripheral oxygen (SpO2) module, a non-invasive blood pressure (NIBP) module, a SureTemp thermometry module, a Braun thermometry module, a printer, an accessory power management stand that can contain extra battery power, USB ports and work surface, a barcode reader, a nurse call, a Newmar radio, a weight scale, a touch screen, a speaker, and a buzzer.

Example hardware 610 that can interact with the LAV system 500 can include a Domain Name System (DNS) server to acquire service IPs, a Dynamic Host Configuration Protocol (DHCP) server to acquire IP addresses, a Network Time Protocol (NTP) server to acquire coordinated universal time (UTC), and an NRS service to acquire a service IPs.

Example services 620 can acquire software error logs, event logs and device configuration. The example services 620 can include a service monitor and a service tool. In embodiments, the service monitor or service tool can be a software application that can interface with the peripheral 600 or hardware 610 to perform software upgrades and download service information from the device.

Reusable assets 502 can include reusable components 504 with reusable capabilities 506. Generally, a reusable capability 506 can be an abstract interface definition that describes the functionality a software item will provide to the software system. Generally, a reusable component 504 can be a software item designed to plug into a software system and provide a set of functionality. Reusable components 504 can implement a reusable capability 506 by conforming to a specific interface.

Figure 5:
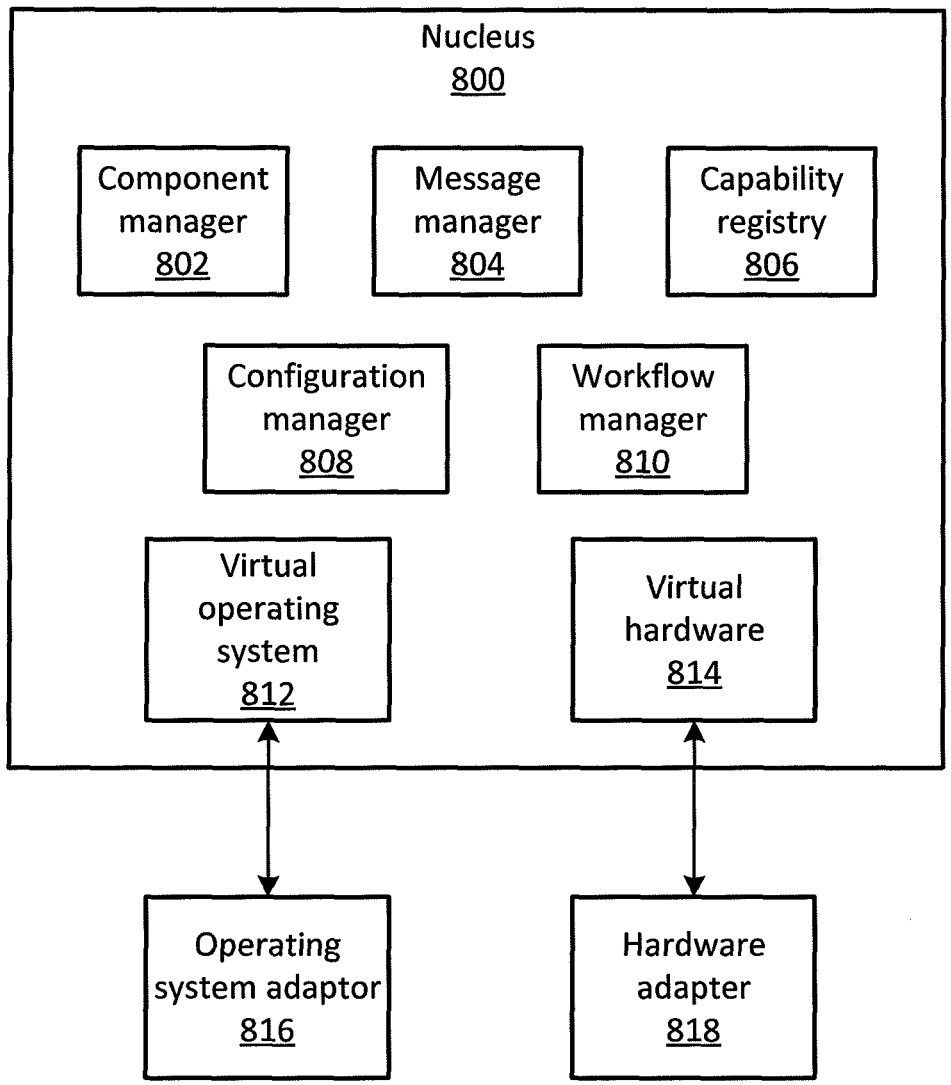
FIG. 5 illustrates the components of an example embodiment of the nucleus.

Examples of the reusable assets 502 include an SpO2 proxy for interfacing with an SpO2 module, an NIBP proxy for interfacing with a NIBP module, a SureTemp proxy for interfacing with a SureTemp thermometry module, a Braun Temperature proxy for communicating with a Braun thermometry module, an audio manager including a set of sound files and that can control the audio hardware for a speaker and/or a buzzer, a Newmar Manager for configuring, controlling and monitoring information about a Newmar radio, an heart rate/pulse rate derived channel that can specify a channel of common object-oriented architecture (COOA) messages that are derived from the output of either or both the NIBP or SpO2 modules, and an off-the-shelf board support that includes drivers for standard and LAV-specialized hardware, which can include the Hardware Adapter that implements the virtual hardware 814 API shown and described in more detail in FIG. 5 below, EEPROM, USB client, Ethernet, touch screen and a light sensor. As used herein, COOA is a software architecture that can incorporate an object-oriented data model with a publish/subscribe bus architecture, and it can be used to communicate information between software items.

Example base Linux system 510 components can include off-the-shelf software products such as Sqlite3, syslog-ng, package manager, QT libraries, NTP client, Python interpreter, U-Boot, Linux kernel and MLO. Additional components of the example base Linux system 510 are possible.

The example nucleus 800 is a set of portable and reusable software items designed to provide a base set of functionality for all, or substantially all, embedded medical devices that use the LAV architecture 500. The example nucleus is shown and described in more detail with reference to FIG. 5 below.

Applications 508 are program modules 1724 that are stored in a mass storage device 1714. Example applications 508 in the LAV software system 500 can include a power manager, a connectivity manager, a patient data manager, a user interface, a barcode manager, an alarms manager, a weight app manager, a log manager, a host proxy, a configuration application, a scale handler, a time manager, a system controller, a debug interface, a service monitor proxy, a software update component, a Bluetooth™ manager, a printer manager, and a peripheral interface controller (PIC) proxy.

Some of the applications 508 can interface with hardware or external components. For example, the power manager can communicate with the power control of the computing device 1700; the barcode manager can interface with a supported barcode reader to receive and publish data and control the power state of the barcode reading; the alarms manager can receive all alarm notifications and interface with the nurse call hardware; the scale handler can interface with an external weight scale; the Bluetooth™ manager can control the interface to the Bluetooth™ module; the user interface module can communicate with an external display, such as a touch-sensitive LCD display; the printer manager can interface with a printer; and the PIC proxy can interface with a PIC processor to receive battery and change information and set LED status on the optional accessory power management stand (APM).

FIG. 5 is a block diagram of the components in an example embodiment of the nucleus 800. The example embodiment 800 includes a component manager 802, a message manager 804, a capability registry 806, a configuration manager 808, a workflow manager 810, a virtual operating system 812 that interfaces with an operating system adaptor 816, and a virtual hardware 814 component that interfaces with a hardware adapter 818. The nucleus 800 is a cross-product, portable framework that can support embedded medical device development. Other embodiments may include more or fewer components of the nucleus 800.

In some embodiments, the component manager 802 can start up the software system including the nucleus 800 and LAV 500 software items, except the Linux kernel, the board support package and the software items started up by the init scripts or before the init program is executed. The example component manager 802 can also shut down the system and perform process monitoring for stuck or failed software items that have registered for process monitoring with the component manager 802.

In embodiments, the component manager 802 can start up the other nucleus 800 software components. Then the component manager 802 can invoke an external application or script to start up the product-specific software components and take any other actions to bring the product to a normal run state. Also, the example component manager 802 can provide a set of COOA messages that can be used by software components to interact with the component manager 802 as well as a class that can be used by a client to simplify usage of the component manager 802 functionality.

In some embodiments, the message manager 804 can provide an inter-process communications bus for sending COOA messages between software items that communicate using the example nucleus 800 architecture. The software items that can communicate through the message manager 804 can include software items from within the nucleus 800 and those outside the nucleus, provided they can communicate using COOA messages.

In embodiments, the example message manager 804 can support publish/subscribe and directed send messages. Also, in embodiments, the message manager 804 can provide a set of messages to subscribe and unsubscribe for messages as well as a class that can be used by software components to simplify the creation, sending and receiving of messages to and through the message manager 804.

In some embodiments, the capability registry 806 can be a bulletin board system where software items can post COOA messages and receive changes to any information posted. The messages can include information about connected hardware, manufacturer of the hardware, software version, and anything else that could be needed by other software components to make use of the available software and hardware capabilities. The messages can also have unique identifiers. The software items that can use the capability registry 806 for posting messages can include all software items designed to communicate using COOA messages and the software items in the nucleus 800.

In embodiments, the capability information can be posted as COOA-format messages and the information can persist until the system is shut down, the posting software component shuts down, or until another COOA message with the same COOA ID is posted. In some embodiments, a COOA message with the same COOA ID will replace an existing COOA message.

Software components in the example LAV system 500 can subscribe through the message manager 804 for COOA messages which are posted to the capability registry 806. In turn the capability registry 806 can publish the COOA messages when they are changed or added. In embodiments, an event message is published when a capability is removed and a "SendTo" is used to notify a component when a non-existent capability COOA message is requested.

In embodiments, software components can send a request message to the capability registry 806 when first subscribing for information in the capability registry 806 to get the current state of the COOA messages. The capability registry 806 can use a directed send to send the requested values back to the requestor, which can prevent possible race conditions between requesting components and updating components.

In embodiments, the example configuration manager 808 can maintain persistent configuration of the device and can provide this information to client software components. The configuration manager 808 can persist configuration through power cycles. Also, the configuration manager 808 can manage multiple versions of each configuration COOA message and can return different versions of a configuration message depending upon the requested item. The COOA message version number can be used to support a versioning scheme of the configuration messages so that the software system can be upgraded and downgraded and still be able to receive and understand the configuration messages.

If, in embodiments, the upgraded software then upgrades a configuration message to a new, higher version, the old configuration message can still be available if the software is downgraded. If a change is then made to the upgraded configuration, the configuration manager 808 can opt to not synchronize changes between versions of configuration messages. If the software is downgraded, the configuration manager 808 can use the old values that were in place before the software upgrade even if the subsequent changes are compatible with the old software.

The configuration manager 808 can use product-provided plugins to interface to different types of storage devices. An example is a plug-in that stores data in a regular file for non-permanent configuration and another plug-in that saves data to an EEPROM for permanent configuration and licenses.

Software components that want to receive configuration data can subscribe to the COOA IDs through the message manager 804 as with other data. In embodiments, after a software component has subscribed to configuration messages, it can send a request to the configuration manager 808 to receive the current values. To prevent a potential race condition, software components that own some configuration, in some embodiments, do not publish changes through the message manager 804, but use the store functionality of the configuration manager 808 and allow the configuration manager 808 to publish the change.

In some embodiments, the workflow manager 810 can run programs, including, but not limited to, scripts, to provide dynamically changing functionality to the device. The example workflow manager 810 can add, remove, start and stop programs, including manager scripts, on demand, as well as provide information about managed programs and/or scripts.

In some embodiments, the virtual operating system 812 can be a wrapper layer to provide a fixed application programming interface (API) between software components and the underlying operating system. In embodiments, the operating system adapter 816 can include software that can cause function calls made using the virtual operating system 812 API to result in corresponding function calls in the operating system.

In some embodiments, the virtual hardware 814 can provide a fixed API between software components and the underlying hardware and device drivers. In embodiments, the hardware adapter 818 can include software that can cause function calls made using the virtual operating system 812 API to result in corresponding function calls to the operating system that accesses the underlying hardware. The virtual hardware 814 can enable abstraction of differences across operating system and hardware instances for these functions such that reusable components do not require re-write to access those components.

Figure 6:
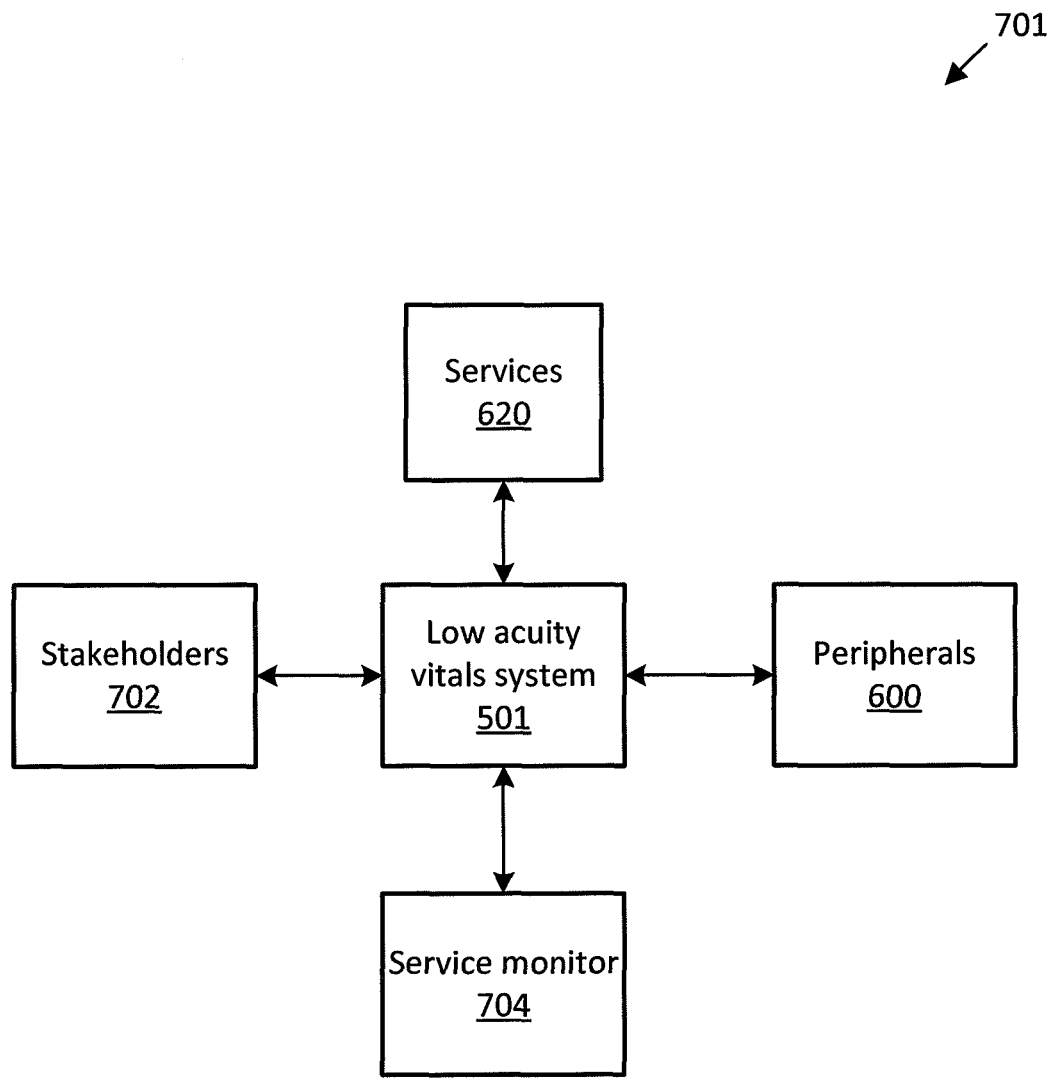
FIG. 6 illustrates an example environment of the low acuity vitals system.

FIG. 6 is a block diagram of an example LAV system environment 701. Included in the example environment 701 is the LAV system 501, which can include services 620 and peripherals 600, stakeholders 702, and a service monitor 704.

Stakeholders 702 include the groups or personnel on the service and customer sides that can interact with the LAV system 501. Example stakeholders 702 can include acquirers, assessors, communicators, developers, maintainers, production engineers, suppliers, support staff, system administrators, testers and users.

The acquirers can include customers who oversee the procurement of the system or product. The assessors can include groups or personnel that oversee the system's conformance to standards and legal regulation. The communicators can explain the LAV system 501 to other stakeholders through documentation and training materials. The developers can construct and deploy the system from specifications. Developers can also be concerned with build standards, platform, language, tools, maintainability, flexibility, and the preservation of knowledge over time.

The maintainers can manage the evolution of the LAV system 501 and can be concerned with system documentation, instrumentation, diagnostics, production change control and the preservation of knowledge over time.

The production engineers can design, deploy and manage the hardware and software environments in which the system can be tested and run, and in which modifications to the system can be built. The suppliers can build and/or supply the hardware, software or infrastructure on which the system runs. The support staff can provide support to users of the system and can be concerned with operational and support issues, such as diagnostics and alerts.

The system administrators can run the system and can be concerned with the system 501 operation including system monitoring, management, disaster recovery, availability, resilience and scalability. The testers can test future builds to ensure they are suitable for use by evaluating the system requirements using tests to prove the requirements have been met. Users can define the system's functionality and can be the people who use the system on a regular basis. Users can be concerned with how the system functions, system performance, operations, security and support. Example users can include healthcare personnel and patients.

In embodiments, personnel and business groups can take on multiple roles, such as service personnel acting as software updater, calibrator, or tester as needed and depending on the actions required. Additional examples of interactions with the LAV system 501 are provided below.

The example LAV system 501 can acquire vital signs from a patient. For example, the patient can have blood pressure measured with a NIBP device, temperature measured using, for example, a SureTemp or Braun thermometer, SpO2 measured, pulse rate measured from, for example, the NIBP device or SpO2, weight measured through USB or wireless-connected weight scales, and have a patient ID barcode scanned.

In embodiments, a clinician can interact with the LAV system 501 by logging in, authenticating, perform readings, reviewing readings, sending readings and using the nurse call. A clinician can log into a device using name and password, or barcode scan with or without a password. Additionally, a clinician can enter configurable modifiers and/or configurable parameters through a user interface, review historical patient vital signs records, and send selected vital signs records to a networked host system, for instance, electronic medical records or Connex CS.

A configurator can, for example, configure the LAV system 501 using a USB drive containing a configuration file or via a wired or wireless network. Additionally, a configurator can clone a LAV system 501 configuration to a storage device, such as a USB drive, and use that to configure other LAV system 501 devices. A configurator can configure the LAV system 501 through a user interface, which can be patient specific, such as alarm limits, or device settings, such as display brightness.

A calibrator can calibrate devices that use the LAV system 501, such as the NIBP module and weight scale module.

A software developer can interact with the LAV system 501 to develop and/or debug software. This can include writing and maintaining device software and gathering information to improve software performance.

A tester can also interact with the LAV system 501. The example tester can prepare test plans, create test tools, execute test plans, review test results, perform unit and integration testing, and test network connectivity, for example, using a ping or traceroute.

Figure 7:
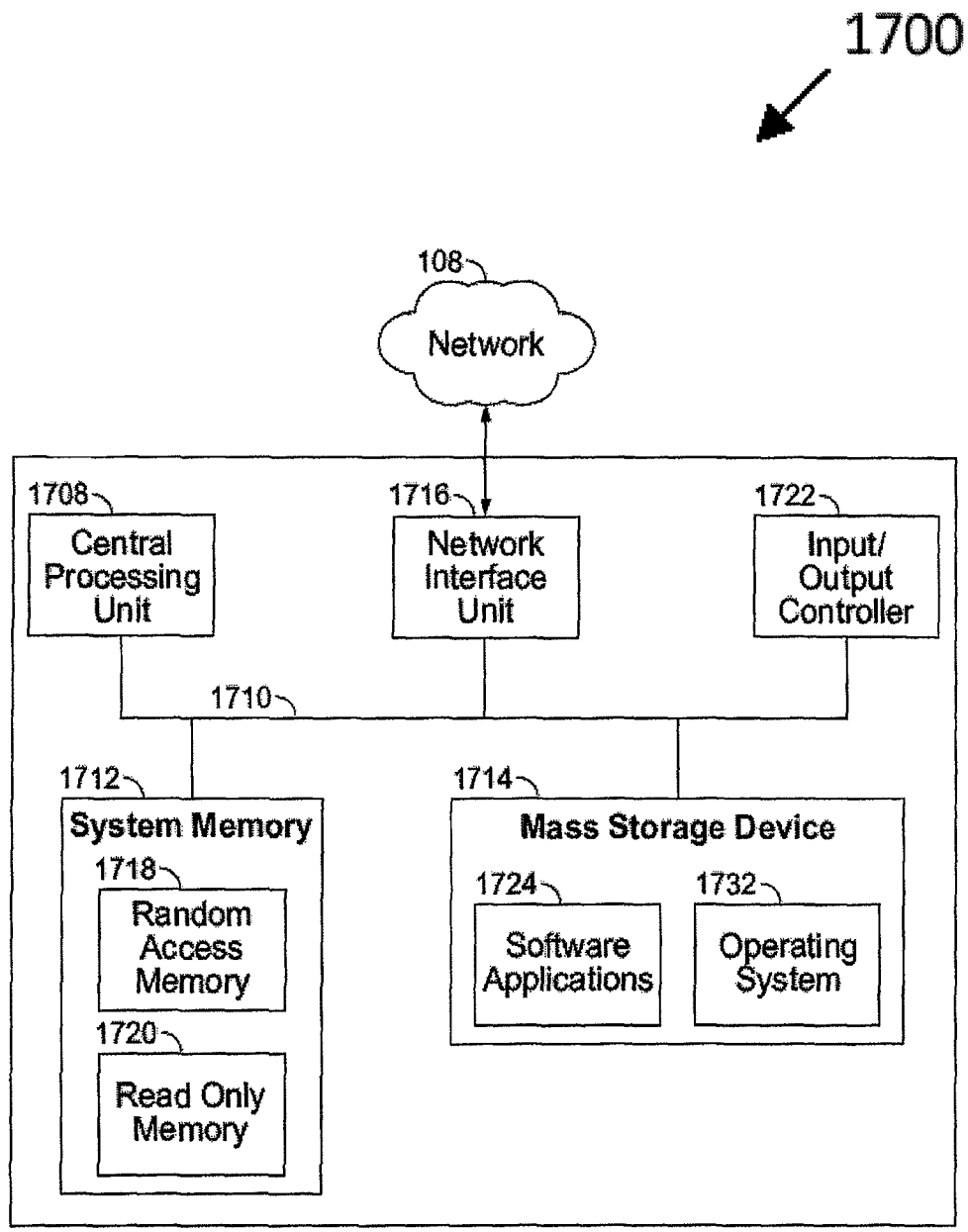
FIG. 7 illustrates example components of a medical device of the system of FIG. 1.

FIG. 7 illustrates example physical components of a computing device, such as the medical devices 102, 104. As illustrated, the device includes at least one central processing unit ("CPU") 1708, a system memory 1712, and a system bus 1710 that couples the system memory 1712 to the CPU 1708. The system memory 1712 includes a random access memory ("RAM") 1718 and a read-only memory ("ROM") 1720. A basic input/output system containing the basic routines that help to transfer information between elements within the device, such as during startup, is stored in the ROM 1720. The device further includes a mass storage device 1714. The mass storage device 1714 is able to store software instructions and data.

The mass storage device 1714 is connected to the CPU 1708 through a mass storage controller (not shown) connected to the bus 1710. The mass storage device 1714 and its associated computer-readable data storage media provide non-volatile, non-transitory storage for the device. Although the description of computer-readable data storage media contained herein refers to a mass storage device, such as a hard disk or CD-ROM drive, it should be appreciated by those skilled in the art that computer-readable data storage media can be any available non-transitory, physical device or article of manufacture from which the device can read data and/or instructions.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the device.

According to various embodiments of the invention, the device may operate in a networked environment using logical connections to remote network devices through the network 108, such as a local network, the Internet, or another type of network. The device connects to the network 108 through a network interface unit 1716 connected to the bus 1710. The network interface unit 1716 may also be utilized to connect to other types of networks and remote computing systems. The device also includes an input/output controller 1722 for receiving and processing input from a number of other devices, including a keyboard, a mouse, a touch user interface display screen, or another type of input device. Similarly, the input/output controller 1722 may provide output to a touch user interface display screen, a printer, or other type of output device.

As mentioned above, the mass storage device 1714 and the RAM 1718 of the device can store software instructions and data. The software instructions include an operating system 1732 suitable for controlling the operation of the device. The mass storage device 1714 and/or the RAM 1718 also store software instructions, that when executed by the CPU 1708, cause the device to provide the functionality of the device discussed in this document. For example, the mass storage device 1714 and/or the RAM 1718 can store software instructions that, when executed by the CPU 1708, cause the physiological monitor device to display the home screen and other screens.

Although the example medical devices described herein are devices used to monitor patients, other types of medical devices can also be used. For example, the different components of the CONNEX™ system, such as the intermediary servers that communicate with the monitoring devices, can also require maintenance in the form of firmware and software updates. These intermediary servers can be managed by the systems and methods described herein to update the maintenance requirements of the servers.

Embodiments of the present invention may be utilized in various distributed computing environments where tasks are performed by remote processing devices that are linked through a communications network in a distributed computing environment.

The block diagrams depicted herein are just examples. There may be many variations to these diagrams described therein without departing from the spirit of the disclosure. For instance, components may be added, deleted or modified.

While embodiments have been described, it will be understood that those skilled in the art, both now and in the future, may make various improvements and enhancements can be made.

What is claimed is:

1. A medical software package stored on a non-transitory, computer-readable storage medium, comprising:

a plurality of software components programmed to provide one or more functionalities to one or more medical monitoring devices;

wherein each of the plurality of software components is programmed to run independently as a daemon;

wherein each of the plurality of software components is programmed to be modified without recompiling unchanged software components;

wherein the plurality of software components is programmed to communicate to each other through at least one of the plurality of software components;

wherein the medical software package is hardware agnostic and operating system agnostic;

wherein the plurality of software components further comprise a plurality of reusable assets;

wherein one of the plurality of reusable assets is a workflow manager programmed to store, add, remove, start, and stop manager programs resident in the non-transitory, computer-readable storage medium;

wherein one of the plurality of reusable assets is a capability registry programmed to provide a bulletin board system where software components can post common object-oriented architecture messages and receive messages about changes to the posted common object-oriented architecture messages;

wherein one of the plurality of reusable assets is a message manager programmed to provide an inter-process communications bus for sending common object-oriented architecture messages between the plurality of software components;

wherein at least one of the posted common object-oriented architecture messages that is sent through the message manager includes a unique identifier and persists on the bulletin board system until another common object-oriented architecture message with the same unique identifier is posted to the bulletin board system;

wherein one of the plurality of reusable assets is a configuration manager programmed to maintain persistent configuration of the one or more medical monitoring devices and provide a device configuration to a plurality of client software components;

wherein one of the plurality of reusable assets is a component manager programmed to start up and shut down at least one of the plurality of software components;

wherein the plurality of reusable assets form a single architecture that includes a set of portable and reusable software items designed to provide a base set of functionality for the one or more medical monitoring devices;

wherein one of the plurality of reusable assets is a virtual operating system programmed to provide a fixed application programming interface between the single architecture and an underlying operating system;

wherein one of the plurality of reusable assets is a virtual hardware programmed to provide a fixed application programming interface between the single architecture and underlying hardware and device drivers; and wherein the single architecture includes the workflow manager, the capability registry, the message manager, the configuration manager, the component manager, the virtual operating system, and the virtual hardware.

2. The medical software package of claim 1, wherein the common object-oriented architecture messages persist on the bulletin board system until a system supporting the medical software package shuts down, or a reusable asset that posted a common object-oriented architecture message shuts down.

3. The medical software package of claim 2, wherein the common object-oriented architecture messages include information about one of the following: connected hardware, hardware manufacturer, and software version.

4. The medical software package of claim 1, wherein the configuration manger is programmed to persist configuration-based common object-oriented architecture messages through power cycles, and wherein the configuration manager is programmed to manage multiple versions of each configuration-based common object-oriented architecture message.

* * * * *